United States Patent
Aronovich et al.

(10) Patent No.: US 9,610,331 B2
(45) Date of Patent: Apr. 4, 2017

(54) METHODS FOR HEMATOPOIETIC PRECURSOR MOBILIZATION

(75) Inventors: Anna Aronovich, Rehovot (IL); Dalit Tchorsh-Yutsis, Rehovot (IL); Gideon Rechavi, Tel-Aviv (IL); Yair Reisner, Old Jaffa (IL)

(73) Assignees: Yeda Research and Development Co. Ltd., Rehovot (IL); Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 210 days.

(21) Appl. No.: 13/394,854

(22) PCT Filed: Sep. 5, 2010

(86) PCT No.: PCT/IL2010/000726
§ 371 (c)(1),
(2), (4) Date: Mar. 8, 2012

(87) PCT Pub. No.: WO2011/030332
PCT Pub. Date: Mar. 17, 2011

(65) Prior Publication Data
US 2012/0189574 A1 Jul. 26, 2012

Related U.S. Application Data

(60) Provisional application No. 61/240,327, filed on Sep. 8, 2009.

(51) Int. Cl.
| | | |
|---|---|---|
| *A61K 38/37* | (2006.01) | |
| *A61K 38/36* | (2006.01) | |
| *A61K 31/4439* | (2006.01) | |
| *A61K 31/727* | (2006.01) | |
| *A61K 38/18* | (2006.01) | |

(52) U.S. Cl.
CPC ........ *A61K 38/363* (2013.01); *A61K 31/4439* (2013.01); *A61K 31/727* (2013.01); *A61K 38/1816* (2013.01); *A61K 38/37* (2013.01)

(58) Field of Classification Search
None
See application file for complete search history.

(56) References Cited

U.S. PATENT DOCUMENTS

| | | | |
|---|---|---|---|
| 6,093,399 A * | 7/2000 | Thorpe et al. | 424/182.1 |
| 8,003,096 B2 * | 8/2011 | Carmeliet et al. | 424/94.63 |
| 2006/0210532 A1 * | 9/2006 | Carmeliet et al. | 424/85.1 |
| 2008/0305097 A1 | 12/2008 | Lapidot et al. | |

FOREIGN PATENT DOCUMENTS

| | | |
|---|---|---|
| WO | WO 2006/048862 | 5/2006 |
| WO | WO 2010/013231 | 2/2010 |
| WO | WO 2011/030332 | 3/2011 |

OTHER PUBLICATIONS

Austin et al.,Blood. Jan. 17, 2013;121(3):431-9. doi: 10.1182/blood-2012-09-355958. Epub Oct. 18, 2012.*
Trejo, J., J Pharmacol Exp Ther. Nov. 2003;307(2):437-42. Epub Sep. 9, 2003.*
Presentation by Tsvee Lapidot on Jan. 27, 2012 at the 27th Annual Meeting of the Belgian Hematological Society in Liege, Belgium, 30 pages.*
Gur-Cohen et al., 53rd ASH Annual Meeting and Exposition, Dec. 11, 2011, poster 2341, abstarct only.*
Levine et al., Am J Pathol 74: 171-178, 1974.*
Ganti et al., J Thromb Thrombolysis (2007) 23:155-158.*
Moskowitz, C. Seminars in Oncology, vol. 31, No. 2 Suppl 4 Apr. 2004: pp. 54-59.*
Nademanee et al., Clinical Lymphoma, vol. 1, No. 1, pp. 46-54, 2000.*
Chuang et al., J. Biol. Chem. 276 (18): 14961-14971.*
Rosencher et al., Arch Cardiovasc Dis. Apr. 2009;102(4):327-33. doi: 10.1016/j.acvd.2009.02.007. Epub Apr. 5, 2009.*
Cashen et al., Bone Marrow Transplant. May 2007;39(10):577-88. Epub Mar. 19, 2007.*
Buckley et al.,Drugs. Sep. 1992;44(3):465-97. (abstract only).*
MacFarlane et al., J Clin Pathol. Feb. 1953;6(1):3-8.*
Reik et al. J Clin Apher. 1997;12(1):10-3.*
Korbling et al., Bone Marrow Transplant. Nov. 1996;18(5):885-90.*
Simonis et al., Biochemistry. May 22, 2007;46(20):6156-64. Epub Apr. 26, 2007.*
Sun et al., Proc Natl Acad Sci U S A. Jun. 23, 1998;95(13):7597-602.*
International Search Report and the Written Opinion Dated Apr. 12, 2011 From the International Searching Authority Re. Application No. PCT/IL2010/000726.
Devine et al. "Mobilization of Hematopoietic Stem Cells for Use in Autologous Transplantation", Clinical Journal of Oncology Nursing, XP002629878, 14(2): 212-222, Apr. 2010.
Fu et al. "Mobilization of Hematopoietic Stem Cells", Haematological Oncology, Blood Reviews, XP002629876, 14: 205-218, 2000. p. 207, Table 1.
Greenbaum et al. "Mechanisms of G-CSF-Mediated Hematopoietic Stem and Progenitor Mobilization", Leukemia, XP002629877, 25(2): 211-217, Feb. 2011. p. 207, Table 1.
Lévesque et al. "Mobilization by Either Cyclosphamide or Granulocyte Colony-Stimulating Factor Transforms the Bone Marrow Into a Highly Proteolytic Environment", Experimental Hematology, XP002629875, 30(5): 440-449, May 2002. Abstract.
Takamatsu et al. "Thrombocytopenia in Association With Splenomegaly During Granulocyte-Colony-Stimulating Factor Treatment in Mice Is Not Caused by Hypersplenism and Is Resolved Spontaneously", Transfusion, XP002629874, 47(1): 41-49, Jan. 2007.
Communication Pursuant to Article 94(3) EPC Dated Feb. 13, 2013 From the European Patent Office Re. Application No. 10768075.3.
Merck "Principles of Cancer Therapy", The Merck Manual of Diagnosis and Therapy, 18th Ed., Chap.149: 1157-1171, 2006.

* cited by examiner

*Primary Examiner* — Michael Szperka

(57) ABSTRACT

Methods of modulating mobilization of cells from the bone marrow are provided. In a specific embodiment there is provided a method of increasing mobilization of hematopoietic precursors from the bone marrow to the peripheral blood in a subject in need thereof, the method comprising: (a) administering to the subject an agent which downregulates an activity or expression of a coagulation factor or an effector thereof; and (b) harvesting the hematopoietic precursors from the peripheral blood.

11 Claims, 4 Drawing Sheets

SEQUENCE LISTING

<160> NUMBER OF SEQ ID NOS: 9

<210> SEQ ID NO 1
<211> LENGTH: 12
<212> TYPE: PRT

-continued

```
<213> ORGANISM: Artificial sequence
<220> FEATURE:
<223> OTHER INFORMATION: PAR1 antagonist peptide
<220> FEATURE:
<221> NAME/KEY: misc_feature
<222> LOCATION: (1)..(1)
<223> OTHER INFORMATION: palmitoylated residue

<400> SEQUENCE: 1

Arg Cys Leu Ser Ser Ser Ala Val Ala Asn Arg Ser
1               5                   10

<210> SEQ ID NO 2
<211> LENGTH: 10
<212> TYPE: PRT
<213> ORGANISM: Artificial sequence
<220> FEATURE:
<223> OTHER INFORMATION: PAR4 antagonist peptide
<220> FEATURE:
<221> NAME/KEY: misc_feature
<222> LOCATION: (1)..(1)
<223> OTHER INFORMATION: palmitoylated residue

<400> SEQUENCE: 2

Ser Gly Arg Arg Tyr Gly His Ala Leu Arg
1               5                   10

<210> SEQ ID NO 3
<211> LENGTH: 20
<212> TYPE: DNA
<213> ORGANISM: Artificial sequence
<220> FEATURE:
<223> OTHER INFORMATION: An exemplary antisense oligonucleotides
      targeted against the Factor VIII mRNA

<400> SEQUENCE: 3
gtccacttgc agccactctt                                              20

<210> SEQ ID NO 4
<211> LENGTH: 19
<212> TYPE: DNA
<213> ORGANISM: Artificial sequence
<220> FEATURE:
<223> OTHER INFORMATION: An exemplary antisense oligonucleotides
      targeted against the Factor VIII mRNA

<400> SEQUENCE: 4
gtccacttgc agccactct                                               19

<210> SEQ ID NO 5
<211> LENGTH: 21
<212> TYPE: DNA
<213> ORGANISM: Artificial sequence
<220> FEATURE:
<223> OTHER INFORMATION: An exemplary antisense oligonucleotides
      targeted against the Factor VIII mRNA

<400> SEQUENCE: 5
gtccacttgc agccactctt t                                            21

<210> SEQ ID NO 6
<211> LENGTH: 19
<212> TYPE: DNA
<213> ORGANISM: Artificial sequence
<220> FEATURE:
<223> OTHER INFORMATION: An exemplary antisense oligonucleotides
      targeted against the Factor VIII mRNA

<400> SEQUENCE: 6
```

```
gctttactct ccattccca                                              19

<210> SEQ ID NO 7
<211> LENGTH: 20
<212> TYPE: DNA
<213> ORGANISM: Artificial sequence
<220> FEATURE:
<223> OTHER INFORMATION: An exemplary antisense oligonucleotides
      targeted against the Factor VIII mRNA

<400> SEQUENCE: 7
tgctttactc tccattccca                                             20

<210> SEQ ID NO 8
<211> LENGTH: 5
<212> TYPE: PRT
<213> ORGANISM: Artificial sequence
<220> FEATURE:
<223> OTHER INFORMATION: PAR1 agonistic peptide
<220> FEATURE:
<221> NAME/KEY: misc_feature
<222> LOCATION: (5)..(5)
<223> OTHER INFORMATION: C'-Amide

<400> SEQUENCE: 8

Thr Phe Leu Leu Arg
1               5

<210> SEQ ID NO 9
<211> LENGTH: 6
<212> TYPE: PRT
<213> ORGANISM: Artificial sequence
<220> FEATURE:
<223> OTHER INFORMATION: PAR4 agonistic peptide
<220> FEATURE:
<221> NAME/KEY: misc_feature
<222> LOCATION: (6)..(6)
<223> OTHER INFORMATION: C'-Amide

<400> SEQUENCE: 9

Ala Tyr Pro Gly Lys Phe
1               5
```

METHODS FOR HEMATOPOIETIC PRECURSOR MOBILIZATION

RELATED APPLICATIONS

This application is a National Phase of PCT Patent Application No. PCT/IL2010/000726 having International filing date of Sep. 5, 2010, which claims the benefit of priority of U.S. Provisional Patent Application No. 61/240,327 filed on Sep. 8, 2009. The contents of the above applications are all incorporated herein by reference.

FIELD AND BACKGROUND OF THE INVENTION

The present invention, in some embodiments thereof, relates to hematopoietic precursor cells mobilization.

The forced migration of hematopoietic stem/progenitor cells (HSPC) from the bone marrow (BM) into the peripheral blood (PB), termed mobilization, is important from a clinical point of view as a procedure that allows for the collection of HSPC for transplantation.

Many agents have been described that induce mobilization of HSPC. Granulocyte-colony stimulating factor (G-CSF), most frequently employed in the clinic, efficiently mobilizes HSPC after a few consecutive daily injections. Other compounds, such as polysaccharides (e.g., zymosan), mobilize HSPC within 1 hour after a single injection. Mobilization can also be induced by chemokines (e.g., IL-8, Gro-β), growth factors (e.g., vascular endothelial growth factor) and CXCR4 antagonists (e.g., AMD3100) and is modulated by lipopolysaccharide that is released by intestinal bacteria. Unfortunately, about 25% of patients do not respond efficiently to currently recommended mobilization protocols and are termed poor mobilizers.

The molecular mechanisms governing the mobilization of HSPC are still not well understood. It was previously shown that expression of the G-CSF receptor (G-CSFR) on hematopoietic progenitor cells (HPCs) is not required for their mobilization into the peripheral blood in response to G-CSF. This observation suggests that G-CSF induces HPC mobilization indirectly through the generation of trans-acting signals. Moreover, accumulating evidence suggests that attenuation of the α-chemokine stromal derived factor-1 (SDF-1)-CXCR4 axis, which plays a pivotal role in retention of HPCs in the BM, results in the release of these cells from the BM into the PB.

It has been demonstrated that a highly proteolytic microenvironment is induced in the bone marrow during HPC mobilization by G-CSF [Levesque et al., Exp Hematol (2002) 30(5):440-9]. In particular, matrix metalloproteinase-9 (MMP-9 or gelatinase B), neutrophil elastase (NE), and cathepsin G (CG) accumulate in the bone marrow of mice during treatment with G-CSF with kinetics that mirror HPC mobilization. Some recent studies suggest that hematopoietic proteases released by neutrophils into the bone marrow microenvironment may play a role in HPC mobilization. Neutrophils express 3 serine proteases: NE, CG, and proteinase 3. These proteases are stored in primary granules of neutrophils and can be released following neutrophil activation [Borregaard and Cowland, Blood. (1997) 89(10):3503-21].

An additional known serine protease is thrombin, a 37 kDa protease well known for its role in the blood coagulation cascade. Thrombin is capable of signaling through Protease-activated receptors PARs, which are expressed throughout the body and are known to be involved in vascular responses, embryonic development and malignancies. PARs belong to a family of G-protein-coupled receptors that undergo N-terminal cleavage to reveal a tethered ligand. It has been shown that NE, CG, and PR3 cleave PARs at distinct sites from thrombin and inhibit subsequent thrombin-induced activation of the receptors [Renesto et al., Blood. (1997) 89(6):1944-53; Sambrano et al., The Journal of biological chemistry. (2000) 275 (10): 6819-23].

U.S. Patent Application No. 20080305097 describes the use of cathepsin K (CTK), a cysteine protease, or a cathepsin K inhibitor (CTKI) for stem cell mobilization. Specifically, U.S. Patent Application No. 20080305097 teaches methods of inducing mobilization of stem cells from the bone marrow to the peripheral blood by the use of CTK or, alternatively, methods of increasing retention of stem cells in the bone marrow by the use of CTKI. According to the teachings of U.S. Patent Application No. 20080305097, CTK is capable of specifically inhibiting SDF-1 activity and thereby effecting stem cell mobilization.

SUMMARY OF THE INVENTION

According to an aspect of some embodiments of the present invention there is provided a method of increasing mobilization of hematopoietic precursors from the bone marrow to the peripheral blood in a subject in need thereof, the method comprising: (a) administering to the subject an agent which downregulates an activity or expression of a coagulation factor or an effector thereof; and (b) harvesting the hematopoietic precursors from the peripheral blood.

According to an aspect of some embodiments of the present invention there is provided a use of an agent which downregulates an activity or expression of a coagulation factor or an effector thereof in the manufacture of a medicament for increasing mobilization of hematopoietic precursors for the treatment of a hematological disorder.

According to an aspect of some embodiments of the present invention there is provided a use of an agent which upregulates an activity or expression of a coagulation factor or an effector thereof in the manufacture of a medicament for treating cancer.

According to an aspect of some embodiments of the present invention there is provided a method of treating cancer in a subject in need thereof, the method comprising administering to the subject a therapeutically effective amount of an agent which upregulates an activity or expression of a coagulation factor or an effector thereof, thereby treating the cancer.

According to some embodiments of the invention, the agent is selected from the group consisting of human Factor VIII, recombinant Factor VIII, porcine factor VIII, Factor X, Factor Xa, Prothrombin, Thrombin, activated prothrombin complex, desmopressin (DDAVP), Factor XIII and Factor XIIIa.

According to some embodiments of the invention, the cancer comprises a solid tumor.

According to some embodiments of the invention, the subject is a human subject.

According to some embodiments of the invention, the subject is a donor subject.

According to some embodiments of the invention, the subject is a recipient subject.

According to some embodiments of the invention, the recipient subject is in need of an organ transplantation.

According to some embodiments of the invention, the organ transplantation comprises stem cell transplantation.

According to some embodiments of the invention, the stem cell transplantation is allogeneic with respect to the recipient.

According to some embodiments of the invention, the stem cell transplantation is autologous with respect to the recipient.

According to some embodiments of the invention, the subject has an immune deficiency.

According to some embodiments of the invention, the immune deficiency comprises a hematologic disorder or condition.

According to some embodiments of the invention, the hematologic disorder or condition is a hematologic cancer.

According to some embodiments of the invention, the subject is in need of stem cell transplantation and the administering is effected prior to the transplantation.

According to some embodiments of the invention, the subject is in need of stem cell transplantation and the administering is effected subsequent to the transplantation.

According to some embodiments of the invention, the coagulation factor or an effector thereof is selected from the group consisting of Factor XII, Factor XI, Factor IX, Factor X, Factor Xa, Factor VIII, Factor VII, Prothrombin, Thrombin and PAR.

According to some embodiments of the invention, the coagulation factor or an effector thereof is Thrombin.

According to some embodiments of the invention, the agent is a Thrombin inhibitor.

According to some embodiments of the invention, the Thrombin inhibitor is selected from the group consisting of Clexane and Dabigatran.

According to some embodiments of the invention, the Thrombin inhibitor is Dabigatran.

According to some embodiments of the invention, the agent is a PAR antagonist.

According to some embodiments of the invention, the PAR antagonist is as set forth in SEQ ID NO: 1.

According to some embodiments of the invention, the PAR antagonist is as set forth in SEQ ID NO: 2.

According to some embodiments of the invention, the method further comprising administering a mobilization factor selected from the group consisting of a growth factor, a cytokine, a chemokine and a polysaccharide.

According to some embodiments of the invention, the mobilization factor is G-CSF.

According to some embodiments of the invention, the mobilization factor is administered in conjunction with the agent which downregulates an activity or expression of the coagulation factor or the effector thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
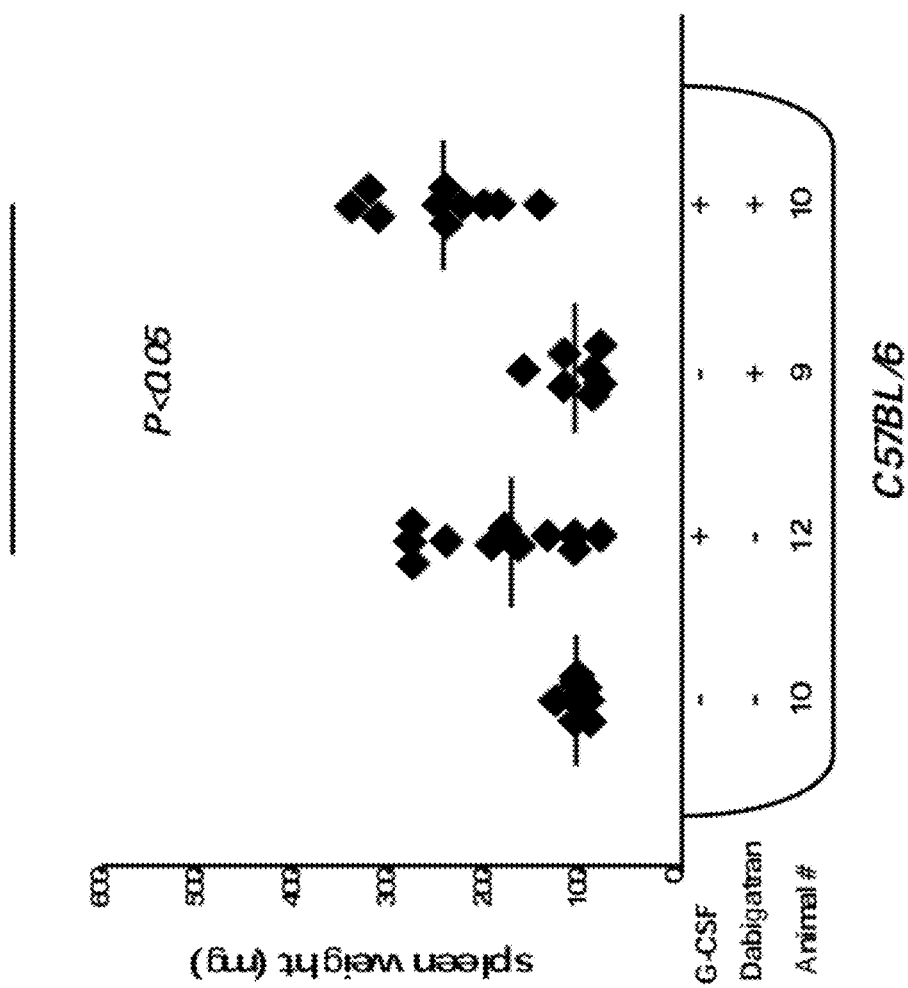
FIG. 1 is a graph depicting splenomegaly in C57BL mice treated with G-CSF with or without Dabigatran. Spleen weights are shown in mg.

The present invention, in some embodiments thereof, relates to methods for hematopoietic precursor mobilization.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Stem cell mobilization from the bone marrow into the peripheral blood is a critical step in the collection of stem cells for transplantation. Unfortunately, about 25% of patients do not respond efficiently to currently recommended mobilization protocols and are termed poor mobilizers.

Previously, it has been suggested that protease activity released from neutrophils into the bone marrow plays a role in stem cell mobilization.

While reducing the present invention to practice, the present inventors have unexpectedly found that thrombin, a serine protease of the blood coagulation cascade, does not induce mobilization as previously believed for other proteases, but rather inhibits stem cells mobilization, probably through PAR signaling. Thus, the present inventors have found that blockade of the coagulation cascade (e.g., upstream of thrombin, or direct inhibition of thrombin by clexane, Dabigatran or PAR antagonists) leads to enhancement of mobilization of hematopoietic precursors.

Accordingly, it is believed that upregulating the coagulation cascade may be beneficial for inhibiting cell mobilization from the bone marrow. It is well known that solid tumors depend on bone marrow-derived cells for tumor vascularization and survival. Also, bone marrow-derived cells can home to distant organs, where they form niches that attract circulating tumor cells. Even more, traffic of leukemic cells from the bone marrow to the periphery may follow similar mechanism to those exhibited by normal hematopoietic stem cells. All these together with the present findings suggest that upregulating a factor of the coagulation cascade or an effector thereof may inhibit bone marrow mobilization and hence may be used for the treatment of cancer.

Thus, according to one aspect of the present invention there is provided a method of increasing mobilization of hematopoietic precursor cells from the bone marrow to the peripheral blood in a subject in need thereof, the method comprising: administering to the subject an agent which downregulates an activity or expression of a coagulation factor or an effector thereof; and harvesting the hematopoietic stem cells from the peripheral blood.

As used herein the term "mobilization" refers to the release of hematopoietic precursors (e.g., stem cells) from bone marrow into peripheral blood circulation.

As used herein "increasing mobilization" refers to inducing mobilization of peripheral blood precursor cells, to elevate circulating levels of peripheral blood precursor cells, or to enhance or facilitate hematopoietic reconstitution or engraftment, in a subject in need thereof.

As used herein "hematopoietic precursors" or "hematopoietic progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies that can be obtained in culture using known protocols. As used herein, "stem" cells are less differentiated forms of progenitor or precursor cells. Typically, such cells are positive for CD34 in humans.

As used herein the term "subject" refers to a mammalian subject e.g., a human subject. The subject may be a healthy subject who serves as a donor for hematopoietic precursor transplantation. Alternatively, the subject may suffer from an immune deficiency and hence is in need of stem cell mobilization or organ e.g., stem cell transplantation (i.e., self-autologous; or from a donor i.e., non-autologous i.e., syngeneic, allogeneic or xenogeneic). In the latter case the subject is a recipient in need of an organ transplant.

Examples of immune deficiencies which can be treated according to the present teachings are provided below.

Typical conditions that can be ameliorated or otherwise benefited by cell mobilization or hematopoietic stem cell transplantation, include, but are not limited to, hematopoietic disorders, such as aplastic anemia, leukemias, drug-induced anemias, and hematopoietic deficits from chemotherapy or radiation therapy. The methods are also useful in enhancing the success of transplantation during and following immunosuppressive treatments as well as in effecting more efficient wound healing and treatment of bacterial inflammation. The methods are also useful for treating subjects who are immunocompromised or whose immune system is otherwise impaired. Typical conditions that are ameliorated or otherwise benefited by the method of the present invention, include those subjects who are infected with a retrovirus and more specifically who are infected with human immunodeficiency virus (HIV). The method thus targets a broad spectrum of conditions for which elevation of progenitor cells and/or stem cells in a subject would be beneficial or, where harvesting of progenitor cells and/or stem cell for subsequent stem cell transplantation would be beneficial. The compounds are also administered to regenerate myocardium by mobilizing bone marrow stem cells.

The methods described herein are also particularly suitable for those subjects in need of repeated or high doses of chemotherapy. For some cancer patients, hematopoietic toxicity frequently limits the opportunity for chemotherapy dose escalation or completion of prescribed chemotherapy. Repeated or high dose cycles of chemotherapy can be responsible for severe stem cell depletion leading to important long-term hematopoietic sequelea and marrow exhaustion. The methods of the present invention provide for improved mortality and blood cell count when used in conjunction with chemotherapy.

In other embodiments the hematological disorder is a hematologic malignancy/cancer such as leukemia and lymphoma.

As mentioned, the method according to this aspect of the present invention is performed by administering to the subject an amount of an agent which downregulates an activity or expression of a coagulation factor or an effector thereof and induces mobilization of hematopoietic precursors from the bone marrow to the blood.

The phrase "coagulation factor" refers to a component of the coagulation cascade including, but not limited to, Factor VIII, Factor VIIIa, Factor V, Factor Va, Factor X, Factor Xa, Prothrombin, Thrombin, Fibrinogen, Factor XIII and Factor XIIIa.

The phrase "an effector of a coagulation factor" refers to a downstream biological pathway regulated by a product of the coagulation cascade such as Protease-Activated Receptor (PAR).

The term "Factor VIII" as used herein refers to coagulation Factor VIII or mimetics thereof such as set forth in GenBank Accession Nos. NP_000123, NM_000132 and NP_063916.

The term "Factor Xa" as used herein refers to coagulation Factor X or mimetics thereof such as set forth in GenBank Accession Nos. NM_000504 and NP_000495.

The term "Thrombin" as used herein refers to coagulation Factor IIa or mimetics thereof such as set forth in GenBank Accession Nos. NM_000506 and NP_000497.

The phrase "Protease-Activated Receptor (PAR)" as used herein refers to the seven transmembrane G-protein-coupled receptor, which is expressed throughout the body (e.g. on platelets, endothelial cells, myocytes and neurons) and is typically activated by the action of serine proteases such as thrombin. Examples of PAR receptors include, but are not limited to, PAR1 e.g. as set forth in GenBank Accession Nos. NM_001992 and NP_001983, PAR2 e.g. as set forth in GenBank Accession Nos. NM_005242 and NP_005233, PAR3 e.g. as set forth in GenBank Accession Nos. NM_004101 and NP_004092 and PAR4 e.g. as set forth in GenBank Accession Nos. NM_003950 and NP_003941.

It will be appreciated that the coagulation factor Factor V includes e.g. GenBank Accession Nos. NM_000130 and NP_000121, the coagulation factor Fibrinogen includes e.g. GenBank Accession Nos. NM_000509, NM_000508, NM_005141, NP_000500, NP_000499 and NP_005132, and the coagulation factor Factor XIII includes e.g. GenBank Accession Nos. NM_001994, NM_000129, NP_001985 and NP_000120.

It will be appreciated that activators of Factor VIII can be modulated according to the present teachings. Examples include, but are not limited to, Factor XII (e.g. GenBank Accession Nos. NM_000505 and NP_000496), Factor XIIa, Factor XI (e.g. GenBank Accession Nos. NM_000128 and NP_000119), Factor XIa, Factor IX (e.g. GenBank Accession Nos. NM_000133 and NP_000124), Factor IXa, protein C (e.g. GenBank Accession Nos. NM_000312 and NP_000303), Von Willebrand factor (vWF, e.g. GenBank Accession Nos. NM_000552 and NP_000543), Factor VII (e.g. GenBank Accession Nos. NM_000131, NM_019616, NP_000122 and NP_062562) and Factor VIIa.

The phrase "activity or expression of a coagulation factor or an effector thereof" as used herein refers to the activity of the coagulation factor or an effector thereof on hematopoietic precursor cell mobilization and may be independent of the coagulation activity of the factor. According to a specific embodiment, the effector is not osteopontin.

Thus, enhancement of mobilization is achieved by down-regulating the expression level and/or activity of a coagulation factor or an effector thereof in the subject. Downregulating the expression level and/or activity of a coagulation factor or an effector thereof can be achieved in any of various ways.

Downregulation of a coagulation factor or an effector thereof can be effected on the genomic and/or the transcript level using a variety of molecules which interfere with transcription and/or translation (e.g., RNA silencing agents, Ribozyme, DNAzyme and antisense), or on the protein level using e.g., antagonists, enzymes that cleave the polypeptide and the like.

Following is a list of agents capable of down-regulating expression level and/or activity of a coagulation factor or an effector thereof.

Downregulation of a coagulation factor or an effector thereof can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to down-regulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The present invention also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target). The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with the present invention can be effected as follows. First, the coagulation factor (e.g. Factor VIII) mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, mouse, rat etc.) using any sequence alignment software, such as the BLAST software available from the NCBI server (wwwdotncbidotnlrndotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, a suitable Factor VIII siRNA can be the siRNA ID s4940, s4941 or s4942 (Ambion Inc., Austin, Tex.).

A suitable Factor X siRNA can be e.g. human F10 Chimera RNAi (Abnova Corporation) and human F10 shRNA (OriGene Technologies).

A suitable Thrombin siRNA can be e.g. human Thrombin R siRNA (Santa Cruz Biotechnology, Inc.).

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide". As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell.

The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIs1, TAT(48-60), pVEC, MTS, and MAP.

Another agent capable of downregulating a coagulation factor (e.g. Factor VIII) is a DNAzyme molecule capable of specifically cleaving an mRNA transcript or DNA sequence of the coagulation factor (e.g. Factor VIII). DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther wwwdotasgtdotorg). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of a coagulation factor or an effector thereof can also be effected by using an antisense polynucleotide capable of specifically hybridizing with an mRNA transcript encoding a coagulation factor or an effector thereof (e.g. Factor VIII, Factor X and Thrombin).

Design of antisense molecules which can be used to efficiently downregulate a coagulation factor or an effector thereof must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published [Matveeva et al., Nature Biotechnology 16: 1374-1375 (1998)].

For example, a suitable antisense oligonucleotides targeted against the Factor VIII mRNA (which is coding for the Factor VIII protein) would be of the following sequences: 5'GTCCACTTGCAGCCACTCTT 3'(SEQ ID NO: 3), 5'GTC CACTTGCAGCCACTCT3'(SEQ ID NO: 4), 5'GTCCACTTGCAGC CACTCTTT 3'(SEQ ID NO: 5), 5'GCTTTACTCTCCATTCCCA 3' (SEQ ID NO: 6), or 5'TGCTTTACTCTCCATTCCCA 3'(SEQ ID NO: 7). An exemplary antisense oligonucleotides targeted against the Factor VIII mRNA Another agent capable of down-regulating a coagulation factor or an effector thereof is a ribozyme molecule capable of specifically cleaving an mRNA transcript encoding a coagulation factor (e.g. Factor VIII). Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

An additional method of regulating the expression of Factor VIII gene and/or genes of other coagulation factors in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonuclotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

```
oligo      3'--A G G T
duplex     5'--A G C T
duplex     3'--T C G A
```

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the Factor VIII regulatory region (or the regulatory region of other coagulation factors or effectors thereof) a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Downregulation of a coagulation factor or an effector thereof can also be effected at the protein level using e.g., antagonists, enzymes. For example, Factor VIII can be down-regulated by, for example, Factor VIII antagonists [e.g. TB-402 (Thromb-X NV)] or Factor VIII inhibitory peptide (e.g. Factor VIII neutralizing antibody). Downregulation of Factor X can be effected using, for example, Clexane, JTV-803 or Fondaparinux. Downregulation of Thrombin can be effected using, for example, Clexane, Dabigatran, Hirudin, Bivalirudin, Lepirudin, Desirudin, Argatroban, Melagatran or ximelagatran.

Another agent which can be used along with the present invention to down-regulate a coagulation factor or an effector thereof is a molecule which prevents a coagulation factor's (e.g. Factor VIII) activation or substrate binding. Such a molecule may comprise an antibody which specifically binds Factor VIII, as for example, sc-73597 [Santa Cruz Biotechnology] or F4.55, F4.77, F4.264, F4.115 and F4.415 [Sola et al., PNAS (1982) 79 (1) 183-187]. Likewise, antibodies which specifically target Factor X (e.g. ab61361, Abcam) or Thrombin (e.g. sc-59716, sc-80590, sc-73475, sc-59717, sc-59718, sc-65961, Santa Cruz Biotechnology) may be used according to the present teachings. Such molecules may also comprise synthetic peptides or antibodies which inhibit PARs, such as for example, the PAR1 agonist TFLLR-NH2 (SEQ ID NO: 8), the PAR4 agonist AYPGKF-NH2 (SEQ ID NO: 9), the palmitoylated peptides pal-RCLSSSAVANRS (SEQ ID NO: 1, PAR1 antagonist) and pal-SGRRYGHALR (SEQ ID NO: 2, PAR4 antagonist).

It will be appreciated that downregulation of a coagulation factor or an effector thereof can also be effected by up-regulating the activity or expression of antithrombin or Protein C.

It will be appreciated that according to the present teachings Vitamin K levels may also be modulated to enhance mobilization of precursor cells.

The above-mentioned agents can be administered alone, or in conjunction with another compound that mobilizes precursor cells, such as a growth factor, a cytokine, a chemokine, a polysaccharide or a drug such as cyclophosphamide or 5-fluorouracil; and/or certain antibodies, such as anti-VLA4. Combinations of these other compounds can also be used.

Examples of mobilization factors which can be used in addition to the above described agents include but are not limited to, Granulocyte-colony stimulating factor (G-CSF) or granulocyte-macrophage colony stimulating factor (GM-CSF) (sargramostim, Berlex, Richmond, Calif.), most frequently employed in the clinic, efficiently mobilizes HSPC after a few consecutive daily injections. Erythropoietin, now commonly used among cancer patients undergoing chemotherapy to maintain hemoglobin in the near normal range, also has some ability to mobilize CD34$^+$ cells. Stem cell factor (SCF) has been shown to be an excellent mobilizing agent, particularly when used in combination with G-CSF. Other compounds, such as polysaccharides (e.g., zymosan), mobilize HSPC within 1 hour after a single injection(10). Mobilization could also be induced by chemokines (e.g., IL-8, Gro-β), growth factors (e.g., vascular endothelial growth factor), and CXCR4 antagonists. Longer lasting variants of G-CSF (pegfilgrastim, Amgen) and erythropoietin (darbopoietin, Amgen) are now available and are in clinical trials as mobilizing agents. They have the benefit of very long half-lives and so add an important measure of patient convenience and the probability that timing of collection may be more flexible without sacrificing optimal collections.

Examples of CXCR4 antagonists include Mozobil (plerixafor) (AnorMED Inc.), AMD-070 (AnorMED Inc.), BKT140 (Biokine Therapeutics Inc.), CXCR4 monoclonal antibody (Northwest Biotechnics Inc.), KRH-2731/CS-3955 (Daiichi Sankyo Company), AVR 118 (reticulose) (Advanced Viral Research Corp.), CXCR4 antagonist (Tai-Gen Biotechnology), and CTCE-0214 (Chemokine Therapeutics Corp).

A new factor (AMD3100, AnorMed, Vancouver, Canada), which is a reversible inhibitor of the binding of stromal derived factor (SDF-1a) to its cognate receptor CXCR4, is currently in clinical trials as a mobilizing agent. It is the first agent to be tried for mobilization based on a rational understanding of its mechanism of action relative to HPC-stromal cell interactions (see Section I). While it mobilizes $CD34^+$ cells adequately on its own, it significantly improves the mobilization capacity of G-CSF when used in combination with G-CSF in mice. Clinical trials in humans with various diseases are in progress, including myeloma.

According to a specific embodiment the agent of the present invention (which decreases activity or expression of a coagulation factor or an effector thereof) is administered with G-CSF.

Agents of the present invention can also be administered with other therapeutically or nutritionally useful agents, such as antibiotics, vitamins, herbal extracts, anti-inflammatories, glucose, antipyretics, analgesics, interleukins (IL-1, IL-2, IL-3, IL-4, IL-5, IL-6, IL-7, IL-8, IL-9, IL-10 IL-11, IL-12, IL-13, IL-14, or IL-15), TPO, or other growth factor such as CSF-1, SF, leukemia inhibitory factor (LIF), or fibroblast growth factor (FGF), as well as C-KIT ligand, M-CSFand TNF-.alpha . . . , PIXY-321 (GM-CSF/IL-3 fusion protein), macrophage inflammatory protein, thrombopoietin, growth related oncogene or chemotherapy and the like.

The agents of the present invention can be provided to a subject in need of organ transplantation (e.g., hematopoietic precursor) prior to, in conjunction with or subsequent to said transplantation/

As mentioned hereinabove, embodiments of the present invention further contemplate upregulating activity of the coagulation cascade for the treatment of cancer.

Thus, according to yet another aspect of the present invention there is provided a method of treating a subject having a cancer (i.e., solid tumor or cancer of the blood), the method comprising administering to the subject a therapeutically effective amount of an agent which upregulates an activity or expression of a coagulation factor or an effector thereof, thereby treating the cancer in the subject.

As used herein a "solid tumor' refers to an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas. Leukemias (cancers of the blood) generally do not form solid tumors.

The present teachings contemplate reducing solid tumor size (e.g., at least by 10%, 20%, 30%, 50%, 60%, 80% or more) such as by inhibiting it's vasculature.

As used herein the term "cancer" refers to any solid or non-solid cancer and/or cancer metastasis, including, but is not limiting to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

Up-regulating the expression level and/or activity of a coagulation factor or an effector thereof (such as those described above) is preferably effected so as to maximally increase the expression level and/or activity of a coagulation factor or an effector thereof in the subject, so as to achieve optimal blockade os cell mobilization from the bone marrow. Up-regulating the expression level and/or activity of a coagulation factor or an effector thereof can be achieved in any of various ways.

For example, upregulation Factor VIII can be effected by administering to the subject human Factor VIII (e.g. plasma-derived Factor VIII), recombinant Factor VIII (e.g. rFVIII, Bayer Biological Products, EU), porcine factor VIII (e.g. HYATE:C), activated prothrombin complex (e.g. APCC, Baxter Healthcare, US) and desmopressin (e.g. DDAVP, Stimate, Minirin). Upregulation of Factor X or Xa may be achieved by administering to the subject the factors per se, available from CalBiochem, La Jolla, Calif. Upregulation of Thrombin may be achieved by administering to the subject Prothrombin or Thrombin, available from CalBiochem, La Jolla, Calif.

It will be appreciated that inhibiting cell mobilization from the bone marrow can also be effected by down-regulating the activity or expression of anti-thrombin.

According to specific embodiments of this aspect of the present invention, other anti-cancer agents or treatment modalities may be provided to the subject to augment the therapeutic effect. These include, but are not limited to, chemotherapy, radiotherapy, biological therapy e.g., immunotherapy.

Each of the agents used for down-regulating or up-regulating a coagulation factor or an effector thereof described hereinabove can be administered to the subject per se or as part of a pharmaceutical composition which also includes a physiologically acceptable carrier. The purpose of a pharmaceutical composition is to facilitate administration of the active ingredient to an organism.

It will be appreciated that the pharmaceutical composition may further comprise other compounds such as described in detail hereinabove.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent which downregulates or upregulates a coagulation factor or an effector thereof. It also refer to other compounds which may be present in the pharmaceutical composition such as the above-mentioned mobilizors, antibiotics. Immunosuppressives etc.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (coagulation factor or an effector thereof upregulating or downregulating agents) effective to modulate transplant organ size of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide adequate levels of the active ingredient as to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The agents will be given for a sufficient amount of time to enablemobilization. Thus, it is advisable to draw a baseline blood sample from each subject prior to administration of the agents of the present invention. Furthermore, once a subject received modulating factors, it is advisable that they return for follow-up evaluation, which include, for example, hematologic and chemical tests for safety.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The method of mobilizing hematopoietic precursor cells can be used for mobilization of stem/progenitor cells in patients who will undergo cytoreductive therapy, such as chemotherapy or radiation therapy. After mobilization, the stem/progenitor cells may be collected from the peripheral blood and either stored, or expanded in culture. The method of mobilizing progenitor cells can also be used for mobilization of precursor cells in individuals who will serve as allogenic donors of progenitor cells. Other diseases and disorders for which the active compound is beneficial in addition to those already described are leukopenia of various origins including, congenital leukopenia, childhood or adult cyclic neutropenia, post-infective neutropenia, and myelodysplastic syndrome. In addition, the active compound can be used for patients who are "difficult to mobilize" because, for example, they are not sensitive to growth factors. The methods can further be used to cause tolerance of a recipient for organ transplantation.

In all of these embodiments, the agents can be administered prior to, simultaneously with, or subsequent to chemotherapeutic exposure.

The methods can additionally be used for gene therapy. Because pluripotent stem cells are self-renewing, and give rise to cell progenitors as well as mature blood cells, the stem cells are an appropriate target for gene therapy. After mobilization, stem/progenitor cells can be collected. The stem/progenitor cells can be modified to deliver gene products upon reintroduction to the individual. After modification, the cells are reinfused into the affected individual.

Any methods including quantitative and qualitative methods can be used to identify that the hematopoietic precursor cells have been mobilized into the peripheral blood. The methods typically involve isolating a quantity of the patient's blood and analyzing the quantity of the cells within the blood. Any method can be used to analyze the number of cells, including but not limited to: ELISA to identify the specific cells, FACS analysis, coulter counters and other blood counting devices, morphological identification, and PCR. The cells can be identified by any method known to one of skill in the art, including but not limited to, the identification of one or more proteins which are specifically expressed by the precursor cells, by morphology, by MRNA expression, and by PCR. The identification of the cells can be done at any time after administration of the agent, included but not limited to: 5 minutes, 10 minutes, 20 minutes, 30 minutes, 45 minutes, 1 hour, 1.5 hours, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days, 7 days, 2 weeks, 1 month, 2 months, 3 months, 4 months, 5 months, 6 months, 7 months, 8 months, 9 months, 10 months, 1 year, 2 years. Further, the mobilization can be identified soon after treatment to identify whether the treatment is working.

The efficacy of the mobilization can be tested throughout treatment with the agents of the present invention, or alternatively, an initial test to determine efficacy can be performed. In one embodiment, a test is performed 1 day after treatment and again 1 week after treatment.

Thus the present invention relates to methods of mobilizing hematopoietic precursors, compositions and articles which comprise agents for mobilizing hematopoietic precursors and uses of these agents in the manufacture of a medicament for increasing mobilization of hematopoietic precursors for the treatment of immune deficiencies such as hematological disorders.

It is expected that during the life of a patent maturing from this application many relevant agents which downregulate or upregulate an activity or expression of a coagulation factor or an effector thereof will be developed and the scope of the term "agent" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

G-CSF Induced Splenomegaly is Enhanced Upon Specific Inhibition of Thrombin

Materials and Experimental Procedures
Animals

All animals were maintained under conditions approved by the Institutional Animal Care and Use Committee at the Weizmann Institute. The study protocol was approved by the ethics committees at Weizmann Institute. In these experiments, 8 to 10 week old immune competent C57BL mice were used. All mice were kept in small cages (up to five animals per cage) and fed sterile food.

G-CSF Treatment

Mice were treated by daily subcutaneous injections of recombinant human G-CSF (Neupogen, Amgen) at a dose of 250 µg per kg per day for 7 days. To determine the spleen weight, mice were euthanized and spleens were harvested 7 days after the initiation of G-CSF treatment.

Treatment with Thrombin Inhibitor

Dabigatran etexilate (Boehringer Ingelheim Pharma KG, Biberach, Germany) was administered orally at a dosage of 30 mg/kg. A final volume of 0.3 ml dissolved in DDW was administered daily.

Results

It was previously shown by Takamatsu et al. [Takamatsu et al., Transfusion. (2007) 47(1): 41-9] that a 7 day daily G-CSF treatment of C57BL/6 mice induced hematopoietic stem cell (HSC) mobilization and splenomegaly. This effect was rarely seen following shorter G-CSF treatments. Thus, G-CSF induced splenomegaly might reflect HSC mobilization.

In order to analyze direct thrombin involvement in HSC mobilization a specific thrombin inhibitor, Dabigatran, was used in conjunction with G-CSF. As can be seen in FIG. 1, Dabigatran administration led to marked enhancement of the G-CSF induced splenomegaly. This result identified thrombin as a potential direct player in the enhanced splenomegaly phenotype (FIG. 1).

Example 2

Enhanced of G-CSF Induced Splenomegaly Upon Specific Inhibition of the Thrombin Receptors PAR1 or PAR4

Materials and Experimental Procedures
Animals

As described in Example 1, hereinabove.

G-CSF Treatment

As described in Example 1, hereinabove.

PAR1 and PAR4 Antagonists

The palmitoylated peptides: pal-RCLSSSAVANRS (PAR1 antagonist, SEQ ID NO: 1) and pal-SGRRYGHALR (PAR4 antagonist, SEQ ID NO: 2) were prepared by solid-phase peptide synthesis using in situ neutralization/HBTU by Hadar Biotec, Israel. The mice were treated by vehicle control, or with PAR1 antagonist or PAR4 antagonist at 0.5 mg/kg, intraperitoneally on daily basis.

Results

Figure 2:
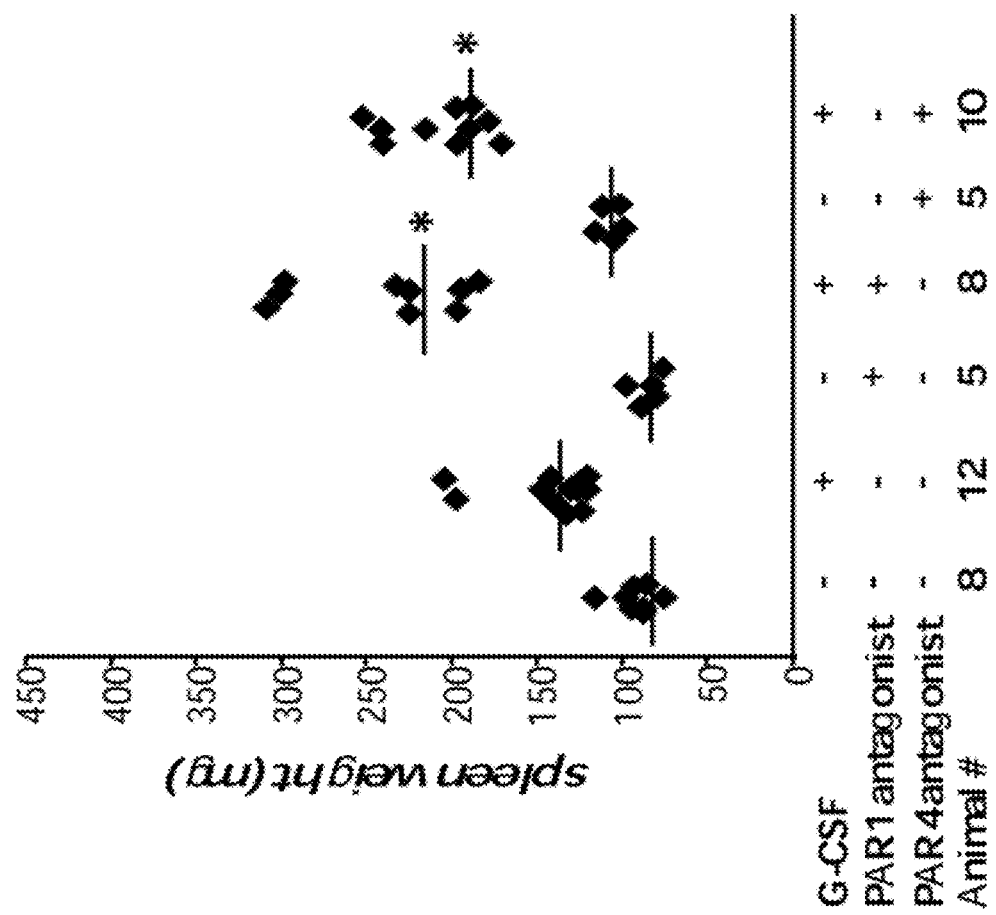
FIG. 2 is a graph depicting G-CSF induced splenomegaly in C57BL mice treated with PAR1 or PAR4 antagonists. Spleen weights are shown in mg.

Since thrombin may operate through PAR signaling and, especially, through a fine balance between PAR1 and PAR4, inventors next evaluated the role of PAR signaling using PAR1 and PAR4 antagonists. As can be seen in FIG. 2, daily treatment with either PAR1 or PAR4 antagonists significantly enhanced G-CSF induced splenomegaly, in a manner similar to the enhancement found in Dabigatran treated mice.

Example 3

Cellular Composition of Spleen and Bone Marrow Under PAR1- and PAR4-Antagonist Administration Materials and Experimental Procedures
Animals
As described in Example 1, hereinabove.
G-CSF Treatment
As described in Example 1, hereinabove.

PAR1 and PAR4 Antagonists
As described in Example 2, hereinabove.

Flow Cytometry Analysis

Membrane expression of different molecules on mouse bone marrow (BM) and spleen cells was detected by flow cytometry, using one- or two-step staining procedures.

Cellular composition of the hematopoietic compartment was stained by CD3-FITC, B220-PE, CD-11b allophycocyanin and Gr-1 FITC ((Pharmigen, BD).

Antibodies for lineage markers CD3, B220, CD11b, Gr-1 and Ten-119 were biotinilated and detected by strepavidine Pe-Cy7, Sca-1 PE and c-Kit—allophycocyanin (Pharmigen, BD).

After staining, cells were washed and analyzed LSRII (Becton Dickinson) using FlowJo software.

Statistical Analysis

Comparisons between the different groups were evaluated using the Student's test. Data were expressed as mean±SD, and were considered statistically significant at p values of 0.05 or less.

Results

To further study the potential mobilization of different cell types to the enlarged spleen following treatment with G-CSF and PAR antagonists, inventors characterized the cellular composition of spleen and bone marrow (BM) before and after treatment (Tables 1 and 2, respectively, below).

TABLE 1

Cellular composition of spleen before and after treatment with G-CSF and PAR antagonists

| Treatment | Animal number | T cells (CD3) | B cells (B220) | Macrophages (CD11b) | Granulocytes (Gr-1) |
|---|---|---|---|---|---|
| None | 5 | 40.052 ± 2.80 | 51.79 ± 2.31 | 3.09 ± 0.54 | 4.586 ± 1.13 |
| PAR1 antagonist | 4 | 39.59 ± 3.41 | 50.57 ± 4.36 | 2.96 ± 1.18 | 3.99 ± 2.42 |
| PAR4 antagonist | 5 | 39.63 ± 3.52 | 46.34 ± 4.23* | 3.53 ± 1.49 | 4.41 ± 2.08 |
| G-CSF | 4 | 34.16 ± 3.17 | 47.37 ± 1.33 | 8.16 ± 2.07 | 10.21 ± 2.69 |
| G-CSF + PAR1 antagonist | 4 | 35.08 ± 0.84 | 46.29 ± 2.46 | 11.36 ± 0.77* | 14.63 ± 1.5* |
| G-CSF + PAR4 antagonist | 4 | 33.07 ± 0.77 | 41.14 ± 2.7* | 11.04 ± 2.54 | 12.8 ± 3.91 |

TABLE 2

Cellular composition of bone marrow before and after treatment with G-CSF and PAR antagonists

| Treatment | Animal number | T cells (CD3) | B cells (B220) | Macrophages (CD11b) | Granulocytes (Gr-1) |
|---|---|---|---|---|---|
| none | 4 | 2.92 ± 1.3 | 19.21 ± 7.63 | 32.34 ± 6.24 | 39.77 ± 3 |
| PAR1 antagonist | 4 | 2.28 ± 0.46 | 13.42 ± 5 | 34.40 ± 5.16 | 38.26 ± 5.31 |
| PAR4 antagonist | 4 | 2.93 ± 1.54 | 16.16 ± 7.26 | 41.06 ± 12.93 | 50.58 ± 9.74 |
| G-CSF | 4 | 0.98 ± 0.85 | 3.18 ± 1.01 | 74.37 ± 7.79 | 77.06 ± 7.38 |
| G-CSF + PAR1 antagonist | 4 | 1.2 ± 0.14 | 2.21 ± 0.41 | 81.15 ± 2.6 | 79.27 ± 2.79 |
| G-CSF + PAR4 antagonist | 4 | 0.29 ± 0.05 | 1.23 ± 0.32* | 73.67 ± 3.83 | 76.17 ± 2.76 |

All values are represented in percentages.
*mean statistically significant.

The data presented in Tables 1 and 2 suggested that a marked elevation of the number of granulocytes and macrophages occurred in both in the BM and spleen after G-CSF treatment, however, in the spleen inventors found a marked synergism with the PAR antagonists, indicating a potential role for PARs in the retention of these cells in the BM and consequently enhanced mobilization upon treatment with PAR antagonists. In contrast, B cell numbers are reduced in both the BM and spleen by the anti-PAR4 antagonist indicating a potential role for PAR4 in B cell proliferation and survival.

Example 4

Mobilization of Hematopoietic Progenitors by G-CSF with or without PAR Antagonists Materials and Experimental Procedures
Animals
All animals were maintained under conditions approved by the Institutional Animal Care and Use Committee at the Weizmann Institute. The study protocol was approved by the ethics committees at Weizmann Institute. In these experiments, 8 to 10 week old immune competent C57BL mice and C57BL hemophilic (C57BL Hem F8) mice were used. All mice were kept in small cages (up to five animals per cage) and fed sterile food.

G-CSF Treatment

As described in Example 1, hereinabove.

PAR1 and PAR4 Antagonists

As described in Example 2, hereinabove.

Colony-Forming Assay

Cells were plated in 0.9% methylcellulose (Sigma Chemical Co.), 30% FCS, DMEM medium (Sigma Chemical Co.), 50 ng/ml stem cell factor (SCF), 5 ng/ml IL-3 (R&D Systems Inc.), 5 ng/ml GM-CSF (R&D Systems Inc.), and 2 U/ml erythropoietin (EPO; Orto Bio Tech, Don Mills, Ontario, Canada). Total spleen cells $5 \times 10^5$ were seeded in semisolid cultures. Colonies were scored 7 days later under an inverted microscope (CK2; Olympus), applying morphological criteria.

Results

Figure 3:
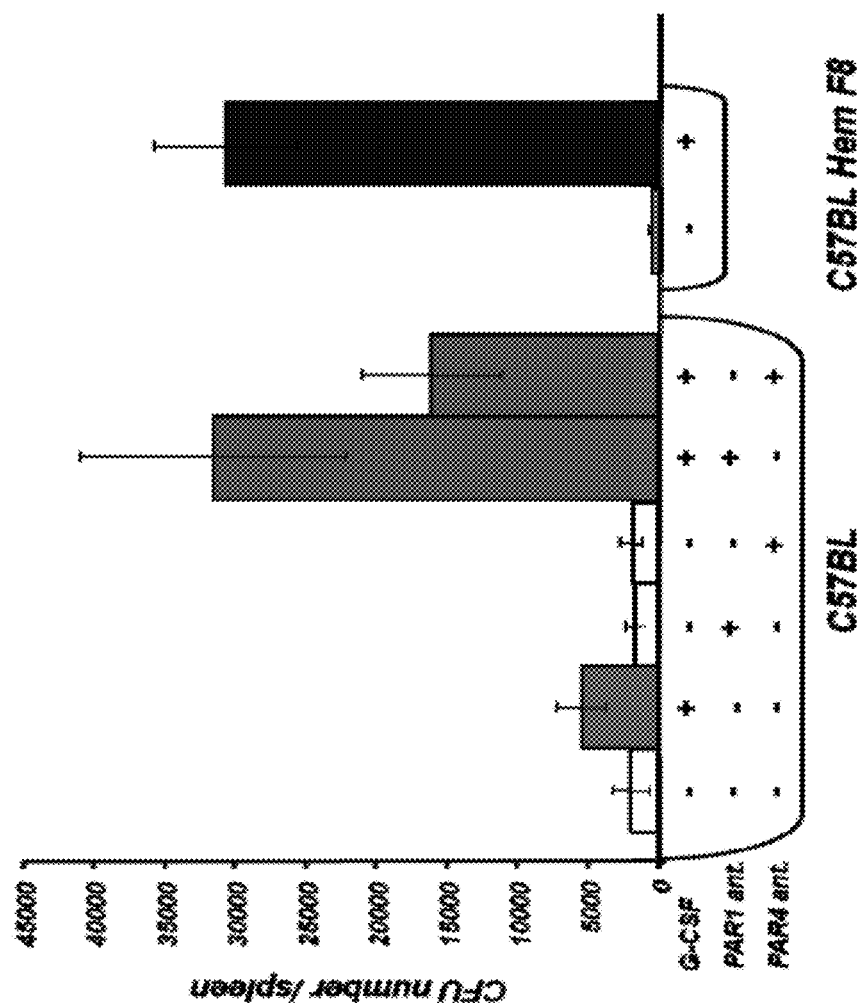
FIG. 3 is a graph depicting enhancement in HPC mobilization following treatment with G-CSF and PAR antagonists. Of note, compared with C57BL/6 mice, C57BL Hemophilic and PAR1- or PAR4-antagonist treated mice had more circulating CFU/spleen at 7 days after G-CSF treatment. $P<0.05$ vs C57BL/6 (n=5).

To study the role of thrombin in the mobilization of hematopoietic progenitors, inventors enumerated these cells by their ability to form colonies in semi-solid media. Thus, after 7 days of treatment with G-CSF with or without PAR antagonists, the number of hematopoietic progenitors in the spleen was estimated by plating the low density mononuclear cells in methylcellulose containing appropriate nutrients and growth factors (see materials and experimental procedures, above). The plates were incubated for 7 days and the colonies were scored using a low magnification microscope. The number of progenitors mobilized into the spleen was presented as CFU/spleen (FIG. 3). As can be seen in FIG. 3, G-CSF treatment alone led to an enhanced mobilization of progenitors by 2.8 fold (as compared to non-treated mice). However, the addition of PAR1 or PAR4 antagonists to G-CSF treatment led to further enhancement of precursor mobilization by 15.3 and 6.4 fold, respectively (as compared to non-treated mice). Likewise, in Factor VIII knock out (KO) mice, which have low thrombin levels due to the absence of Factor VIII, an enhancement of spleen colonies by a factor of 15.9 was recorded upon treatment with G-CSF.

These results strongly suggest that PAR1 and PAR4 antagonists augment G-CSF-mediated mobilization of hematopoietic precursors.

Example 5

Mobilization of Pluripotent Hematopoietic Stem Cells

Materials and Experimental Procedures

Animals

As described in Example 1, hereinabove.

G-CSF Treatment

As described in Example 1, hereinabove.

PAR1 and PAR4 Antagonists

As described in Example 2, hereinabove.

Flow Cytometry Analysis

Membrane expression of different molecules on mouse bone marrow (BM), spleen and peripheral blood (PB) mononuclear cells (MNCs) was detected by flow cytometry, using one- or two-step staining procedures.

Cells were stained for lineage negative Lin– (CD3, B220, CD11b, Gr-1 and Ten-119 were biotinilated and detected by strepavidine Pe-Cy7), stem cell factor receptor positive (c-kit allophycocyanin+), stem cell antigen-1 positive (Sca-1 PE+) using Pharmigen, BD.

After staining, cells were washed and analyzed on LSRII (Becton Dickinson) using FlowJo software.

Statistical Analysis

Comparisons between the different groups were evaluated using the Student's test. Data were expressed as mean±SD, and were considered statistically significant at p values of 0.05 or less.

Results

Figure 4:
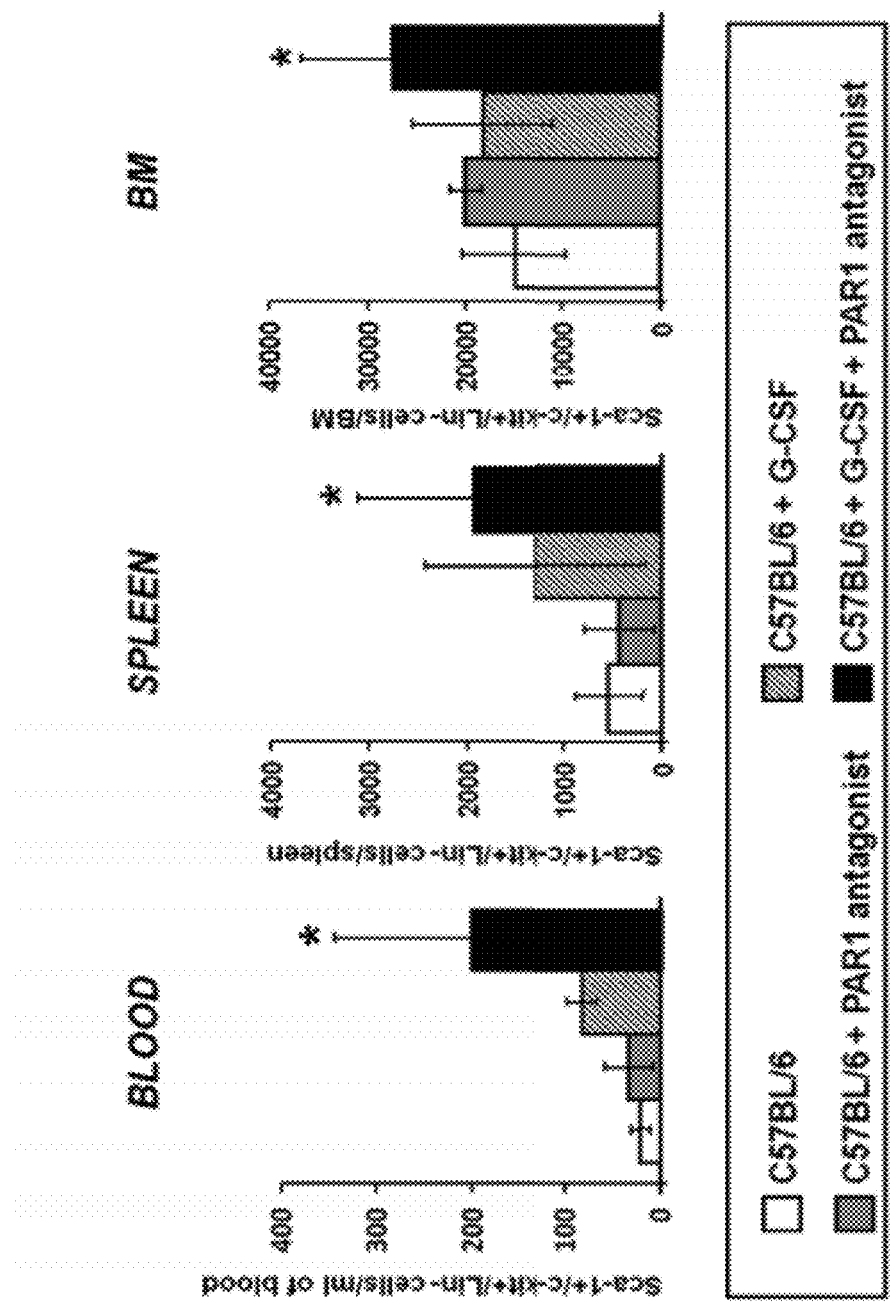
FIG. 4 is a graph depicting enhancement in Lin−Kit+Sca+ stem cell numbers following treatment with G-CSF and PAR1 antagonist. Blood, spleen and BM were evaluated in the differently treated C57BL/6 mice (n=5).

While the CFU assay identified relatively committed precursors, it was possible to identify the more primitive hematopoietic stem cells according to their phenotypic expression of cell surface markers. Thus, lineage negative (Lin–), stem cell factor receptor positive (c-kit+), stem cell antigen-1 positive (Sca-1+) cells were identified in the spleen, BM and blood by FACS analysis before and after treatment with G-CSF and PAR antagonists. As can be seen in FIG. 4, PAR1 co-treatment with G-CSF induced the highest increase in Lin–Kit+Sca+ stem cell number in the blood and the spleen. In addition, this co-treatment clearly enhanced Lin–Kit+Sca+ stem cell numbers in the bone marrow, indicating potential stimulation of proliferation of this population or alternatively enhanced survival. Interestingly, marked enhancement by PAR1 antagonist of Lin–Kit+Sca+ stem cells numbers was found in the blood and especially in the BM even without G-CSF treatment, indicating a role for thrombin in maintenance of hematopoietic stem cell quiescence in the BM.

Collectively these results suggest that thrombin blockade by different inhibitors can enhance hematopoietic stem cell mobilization, especially in conjunction with G-CSF.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of increasing mobilization of hematopoietic precursors from the bone marrow to the peripheral blood in a human subject, wherein the subject has a hematologic disorder or condition that is not Hodgkin's lymphoma, the method comprising:
   (a) administering to the subject Clexane or Dabigatran;
   (b) administering to the subject a mobilization factor comprising G-CSF;
   (c) determining the efficacy of said mobilization; and subsequently
   (d) harvesting said hematopoietic precursors from the peripheral blood, thereby increasing said mobilization of said hematopoietic precursors from said bone marrow to said peripheral blood in said human subject.

2. The method of claim 1, wherein said subject is an autologous recipient subject.

3. The method of claim 1, wherein said subject is in need of stem cell transplantation and said administering is effected prior to said transplantation.

4. The method of claim 1, wherein said subject is in need of stem cell transplantation and said administering is effected subsequent to said transplantation.

5. The method of claim 1, wherein said mobilization factor is administered in conjunction with said Clexane or said Dabigatran.

6. The method of claim 1, wherein said administering is effected in a plurality of administrations, with a course of treatment lasting from several days to several weeks.

7. The method of claim 1, wherein said determining said efficacy of said mobilization is effected by isolating a quantity of the patient's blood and analyzing the quantity of the hematopoietic precursor cells within the blood.

8. A method of increasing mobilization of hematopoietic precursors from the bone marrow to the peripheral blood in a healthy human subject, the method comprising:
   (a) administering to the subject Clexane or Dabigatran;
   (b) administering to the subject a mobilization factor comprising G-CSF;
   (c) determining the efficacy of said mobilization; and subsequently
   (d) harvesting said hematopoietic precursors from the peripheral blood, thereby increasing said mobilization of said hematopoietic precursors from said bone marrow to said peripheral blood in said healthy human subject.

9. The method of claim 8, wherein said mobilization factor is administered in conjunction with said Clexane or said Dabigatran.

10. The method of claim 8, wherein said administering is effected in a plurality of administrations, with a course of treatment lasting from several days to several weeks.

11. A method of increasing mobilization of hematopoietic precursors from the bone marrow to the peripheral blood in a human subject, wherein the subject has a hematologic disorder or condition that is not Hodgkin's lymphoma, the method comprising:
   (a) administering to the subject Clexane or Dabigatran, wherein said administering is effected in a plurality of administrations, with a course of treatment lasting from several days to several weeks;
   (b) administering to the subject a mobilization factor comprising G-CSF; and subsequently
   (c) harvesting said hematopoietic precursors from the peripheral blood, thereby increasing said mobilization of said hematopoietic precursors from said bone marrow to said peripheral blood in said human subject.

\* \* \* \* \*